United States Patent
Staley

(10) Patent No.: US 6,376,223 B1
(45) Date of Patent: Apr. 23, 2002

(54) PROCESS FOR PURIFYING POLYCARBOXYLIC ACIDS

(75) Inventor: Michael D. Staley, Cincinnati, OH (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/631,398

(22) Filed: Aug. 3, 2000

Related U.S. Application Data

(63) Continuation-in-part of application No. 09/624,780, filed on Jul. 25, 2000.
(60) Provisional application No. 60/147,109, filed on Aug. 4, 1999.

(51) Int. Cl.[7] .................................................. C12P 7/40
(52) U.S. Cl. ........................ 435/136; 562/580; 562/582; 562/584; 562/585; 562/589; 562/593; 562/607; 562/608
(58) Field of Search .......................... 435/136; 562/580, 562/582, 584, 585, 589, 593, 607, 608

(56) References Cited

U.S. PATENT DOCUMENTS

| | | |
|---|---|---|
| 259,458 A | 4/1952 | Jenness |
| 5,254,466 A | 10/1993 | Picataggio et al. |
| 5,349,084 A | 9/1994 | Shishikura et al. |
| 5,620,878 A | 4/1997 | Picataggio et al. |

FOREIGN PATENT DOCUMENTS

| | | | |
|---|---|---|---|
| GB | 792487 | | 3/1958 |
| WO | WO-00/20620 | * | 4/2000 |

* cited by examiner

Primary Examiner—Francisco Prats
Assistant Examiner—Kailash C Srivastava
(74) Attorney, Agent, or Firm—John E. Drach

(57) ABSTRACT

Polycarboxylic acids are purified by contacting a crude polycarboxylic acid with a solvent to produce a substantially pure polycarboxylic acid. The solvent is chosen so that the impurities are soluble in the solvent and the polycarboxylic acid is insoluble in the solvent.

10 Claims, No Drawings

PROCESS FOR PURIFYING POLYCARBOXYLIC ACIDS

This application claims the benefit of earlier filed and copending provisional application Serial No. 60/147,109 filed on Aug. 4, 199, and is a CIP of copending application Serial No. 09/624,780 filed on Jul. 25, 2000, the entire contents of which are incorporated herein by reference.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain rights in the invention.

BACKGROUND OF THE INVENTION

This invention relates to a process for purifying a polycarboxylic acid. More specifically, the invention relates to a process for purifying a polycarboxylic acid made by the biological oxidation of a substrate by a microorganism from a fermentation broth.

Aliphatic dioic acids are versatile chemical intermediates useful as raw materials for the preparation of perfumes, polymers, adhesives and macrolid antibiotics. The purity of dicarboxylic acids is critical when they are used to make polyesters because of the dependency of the molecular weight of the polyester on the purity of the dicarboxylic acid. It is well known that maximum molecular weight of a polymer produced by polycondensation will be attained under conditions favoring the most efficient reaction of the functional groups. Such conditions are attained when undesirable side reactions are substantially eliminated through, inter alia, the use of high purity bifunctional reagents. While several chemical routes to the synthesis of long-chain alpha, omega dicarboxylic acids are available, the synthesis is not easy and most methods result in mixtures containing shorter chain lengths. As a result, extensive purification steps are necessary. Dicarboxylic acids, especially long-chain dicarboxylic acids can also be produced by microbial transformation of alkanes, fatty acids or esters thereof. Such syntheses result in dicarboxylic acids having monocarboxylic acid impurities. The presence of monocarboxylic acids can substantially affect the molecular weight of any polycondensation polymer made with dicarboxylic acids having monocarboxylic acid impurities. There is, therefore, a need for methods for preparing highly pure dicarboxylic acids.

SUMMARY OF THE INVENTION

The present invention relates to a process for purifying a polycarboxylic acid. The method comprises contacting a polycarboxylic acid with a solvent to produce a substantially pure polycarboxylic acid. The solvent is chosen so that the impurities are soluble in the solvent and the polycarboxylic acid is insoluble in the solvent.

BRIEF DESCRIPTION OF THE DRAWINGS

Not applicable.

DESCRIPTION OF THE INVENTION

Except in the claims and the operating examples, or where otherwise expressly indicated, all numerical quantities in this description indicating amounts of material or conditions of reaction and/or use are to be understood as modified by the word "about" in describing the broadest scope of the invention.

It is understood that a carboxylic acid is any compound containing one or more carboxyl groups. A polycarboxylic acid is any compound having two or more carboxyl groups.

The present invention relates to a process for purifying a polycarboxylic acid. The method comprises contacting a polycarboxylic acid with a hydrocarbon solvent to produce a substantially pure polycarboxylic acid. The solvent is chosen so that the impurities are soluble in the hydrocarbon solvent and the polycarboxylic acid is insoluble in the solvent. Substantially pure polycarboxylic acids are substantially free of detectable amounts of monocarboxylic acids, mono- and dicarboxylic acid esters, nitrogen-containing materials and, sulfur-containing materials. Typically, substantially pure polycarboxylic acids produced by the process according to the invention contain less than about 2% by weight of detectable amounts of monocarboxylic acids, mono- and dicarboxylic acid esters, nitrogen-containing materials and, sulfur-containing materials.

The process according to the invention can be used to purify any polycarboxylic acid, especially those polycarboxylic acids having monocarboxylic acid impurities as the major impurities. The polycarboxylic acids that can be purified by process according to the invention include aliphatic dicarboxylic acids such as oxalic, malonic, adipic, azelaic, sebacic, dodecanedioc, 1,18-octadecendioic acid and the like; low molecular weight aliphatic tricarboxylic acids such as citric acid; aromatic dicarboxylic acids such as phthalic, isophthalic and terephthalic acids; aromatic dicarboxylic acids such as, trimellitic acid.

The solvent that can be used in the process according to the invention is any aliphatic or aromatic hydrocarbon solvent and/or mixtures thereof in which the monocarboxylic acid impurities present in the crude dicarboxylic acid are soluble and in which the dicarboxylic acid is substantially insoluble. Examples of such aliphatic solvents include, but are not limited to, linear and branched, cyclic and acyclic alkanes such as pentane, hexane, heptane, octane, 2,2,4-trimethylpentane, cyclopentane, cyclohexane, methylcyclopentane, methylcyclohexane; alkenes such as pentene, hexene, heptene, cyclopentene, cyclohexene, methylcyclopentene, methylcyclohexene and the like and liquefied hydrocarbons that are normally gases at room temperature and pressure such as liquid propane and liquid butane. Examples of such aromatic solvents include, but are not limited to, benzene, toluene, xylene. Solvent mixtures include, but are not limited to, petroleum distillates such as naphtha and petroleum ether.

The crude polycarboxylic acid is contacted by the hydrocarbon solvent for an effective time and in an effective amount sufficient to remove substantially all detectable amounts of monocarboxylic acids, mono- and dicarboxylic acid esters, nitrogen-containing materials and, sulfur-containing materials. The contacting can be carried out in any manner that is effective in removing at least the above impurities such as by stirring a slurry of solid crude polycarboxylic acid, passing the hydrocarbon solvent through a zone of solid crude polycarboxylic acid such as a column or tower of solid crude polycarboxylic acid. Liquid crude polycarboxylic acids can be contacted by heating a solid crude polycarboxylic acid and the hydrocarbon solvent until the polycarboxylic acid melts thereby forming two liquid phases which are then intimately contacted such as by stirring. The method of contacting the solid crude polycarboxylic acid with the hydrocarbon solvent and the time required will depend upon the nature of the polycarboxylic acid, the hydrocarbon solvent and the amount and type of impurities in the solid crude polycarboxylic acid and will be readily determinable by those of ordinary skill in the art.

The process according to the invention is particularly useful for purifying long chain aliphatic dicarboxylic acids having long chain monocarboxylic acid impurities. The process is especially useful for the purification of long chain aliphatic dicarboxylic acids produced by fermentation such as by the methods described in U.S. Pat. Nos. 5,254,466 and 5,620,878, the entire contents of each of which are incorporated herein by reference. A particularly preferred embodiment of the process according to the invention is the purification of mixed saturated and unsaturated dicarboxylic acids having primarily oleic acid impurities by contacting the long chain dicarboxylic acids with a hydrocarbon solvent.

The following examples are meant to illustrate but not to limit the invention.

EXAMPLE 1

About 58.46 g of distilled long chain dicarboxylic acids crushed with a mortar and pestle were added to 292 ml of hexane at room temperature. The mixture was allowed to stir for 1.5 hours. The long chain dicarboxylic acids were then removed from the mixture by filtration, washed three times with 100 ml of room temperature hexane and allowed to air dry. The analysis of the starting and final long chain dicarboxylic acids are listed below.

EXAMPLE 2

About 50.16 g of distilled long chain dicarboxylic acids were added to 250 ml of hexane. The mixture was slowly heated with slow stirring until the long chain dicarboxylic acids melted and two layers formed. The mixture was then stirred vigorously to allow as much contact as possible of the two layers. The mixture was then allowed to cool to room temperature. Crystals formed. The crystals were removed by filtration, washed three times with 100 ml of room temperature hexane and allowed to air dry. The analysis of the starting and final long chain dicarboxylic acids are listed below.

|  | Starting long chain Dicarboxylic acids | Contacted long Chain dicarboxylic acids solid state | Contacted long chain dicarboxylic acids liquid state |
|---|---|---|---|
| Acid Value | 332 | 364 | 363 |
| Sap Value | 350 | 366 | 366 |
| Ester Value | 5.1 | .5 | — |
| $N_2$ (ppm) | 185 | 67; 130 | 55; 98 |
| S (ppm) | 115 | 12 | 14 |
| G.C. Analysis, by ISTD |  |  |  |
| 2-Octanol | 2.56 | .12 | .19 |
| C16M | .11 | — | — |
| C16.1M | .11 | .08 | .08 |
| C18M | .10 | — | — |
| C18.1M | 3.44 | .39 | .30 |
| C18.2M | .16 | — | — |
| C20.1M | .29 | — | — |
| C14DI | 3.01 | 3.50 | 3.47 |
| C14.1DI | .36 | .12 | .14 |
| C15DI | .09 | .31 | .28 |
| C16DI | 5.21 | 6.49 | 6.50 |
| C16.1DI | 4.69 | 3.33 | 2.76 |
| C17DI | — | .22 | .20 |
| C17.1DI | .98 | .77 | .90 |
| C18DI | .85 | 1.06 | 1.01 |
| C18.1DI | 72.75 | 84.00 | 83.33 |
| C18.2DI | 3.09 | 1.30 | 1.73 |
| C20.1DI | 1.28 | .97 | .73 |
| TOTAL MONOACIDS | 4.21 | .47 | .38 |
| TOTAL DIACIDS | 92.31 | 102.07 | 101.05 |
| TOTAL | 99.08 | 102.68 | 101.62 |

Ester content is the % of the carboxyl groups that are as esters vs. those that are acid and is defined as Ester %=(SAP Value−Acid Value)/SAP Value×100%.

EXAMPLE 3

About 50.00 g of distilled long chain dicarboxylic acids were added to 250 ml VM&P Naphtha. The mixture was slowly heated to 65° C. with stirring until all the long chain dicarboxylic acid was dissolved. The mix was then allowed to slowly cool to room temperature. Crystals formed. The crystals were removed by filtration. Residual solvent was removed by heat and reduced pressure. The analysis of the starting and final product is listed below.

EXAMPLE 4

About 50.00 g of distilled long chain dicarboxylic acids were added to 250 ml 1-octene. The mixture was slowly heated to 65° C. with stirring until all the long chain dicarboxylic acid was dissolved. The mix was then allowed to slowly cool to room temperature. Crystals formed. The crystals were removed by filtration. Residual solvent was removed by heat and reduced pressure. The analysis of the starting and final product is listed below.

EXAMPLE 5

About 50.00 g of distilled long chain dicarboxylic acids were added to 250 ml 1-decene. The mixture was slowly heated to 65° C. with stirring until all the long chain dicarboxylic acid was dissolved. The mix was then allowed to slowly cool to room temperature. Crystals formed. The crystals were removed by filtration. Residual solvent was removed by heat and reduced pressure. The analysis of the starting and final product is listed below.

| Major Components by Area % G.C. Anaylsis | Starting Long Chain Dicarboxylic Acid Mixture | Recrystallized Long Chain Dicarboxylic Acids in VM&P Naptha | Recrystallized Long Chain Dicarboxylic Acids in 1-octene | Recrystallized Long Chain Dicarboxylic Acids in 1-decene |
|---|---|---|---|---|
| C16 Mono | .12 | .10 | .10 | .08 |
| C16.1Mono | .09 | .11 | .10 | .09 |
| C18Mono | .32 | .26 | .22 | .20 |
| C18.1Mono | 7.42 | 5.30 | 4.73 | 4.35 |
| C18.2Mono | .55 | .36 | .33 | .30 |
| C16Di | 3.69 | 3.91 | 3.87 | 3.81 |
| C18Di | 2.70 | 3.62 | 3.89 | 3.47 |
| C18.1Di | 78.19 | 81.19 | 82.12 | 82.48 |
| C18.2Di | 4.28 | 4.04 | 3.94 | 3.88 |
| Total Monocarboxylic Acids | 8.50 | 6.13 | 5.48 | 5.02 |

-continued

| Major Components by Area % G.C. Anaylsis | Starting Long Chain Dicarboxylic Acid Mixture | Recrystallized Long Chain Dicarboxylic Acids in VM&P Naptha | Recrystallized Long Chain Dicarboxylic Acids in 1-octene | Recrystallized Long Chain Dicarboxylic Acids in 1-decene |
|---|---|---|---|---|
| Total Dicarboxylic Acids | 88.86 | 92.76 | 93.82 | 93.64 |
| Total Carboxylic Acids | 97.36 | 98.89 | 99.30 | 98.66 |

What is claimed is:

1. A process for purifying a polycarboxylic acid comprising the steps of (1) contacting a crude polycarboxylic acid with a sufficient amount of a hydrocarbon solvent and for a sufficient time to form a solution comprised of the hydrocarbon solvent and impurities comprised of monocarboxylic acids, mono- and dicarboxylic acid esters, nitrogen-containing materials and, sulfur-containing materials and a solid comprised of polycarboxylic acid substantially fee of the impurities and, (2) separating the solid from the solution.

2. The process of claim 1 wherein the polycarboxylic acid is an aliphatic dicarboxylic acid.

3. The process of claim 2 wherein the aliphatic dicarboxylic acid is 1,18-octadecendioic acid.

4. The process of claim 1 wherein the hydrocarbon solvent is hexane.

5. The process of claim 1 wherein the solvent is a petroleum distillate.

6. The process of claim 5 wherein the petroleum distillate is naphtha.

7. The process of claim 1 wherein the polycarboxylic acid is 1,18 octadecendioic acid.

8. A process for purifying 1,18-octadecendioic acid comprising the steps of (1) contacting crude 1,18-octadecendioic acid with a sufficient amount of a hydrocarbon solvent and for a sufficient time to form a solution comprised of the hydrocarbon solvent and impurities comprised of monocarboxylic acids, mono- and dicarboxylic acid esters, nitrogen-containing materials and, sulfur-containing materials and a solid comprised of 1,18-octadecendioic acid substantially free of the impurities and, (2) separating the solid from the solution.

9. A process for purifying a polycarboxylic acid comprising the steps of (1) contacting a crude polycarboxylic acid with a sufficient amount of a petroleum distillate and for a sufficient time to form a solution comprised of the petroleum distillate and impurities comprised of monocarboxylic acids, mono- and dicarboxylic acid esters, nitrogen-containing materials and, sulfur containing materials and a solid comprised of polycarboxylic acid substantially free of the impurities and, (2) separating the solid from the solution.

10. A process for purifying 1,18-octadecendioic acid comprising the steps of (1) contacting crude 1,18-octadecendioic acid with a sufficient amount of a naphtha or petroleum ether and for a sufficient time to form a solution comprised of a naphtha or petroleum ether and impurities comprised of monocarboxylic acids, mono- and dicarboxylic acid esters, nitrogen-containing materials and, sulfur-containing materials and a solid comprised of 1,18-octadecendioic acid substantially free of the impurities and, (2) separating the solid from the solution.

* * * * *